United States Patent [19]
Buckley et al.

[11] Patent Number: 5,674,752
[45] Date of Patent: Oct. 7, 1997

[54] CONDUCTIVE POLYMER COATED FABRICS FOR CHEMICAL SENSING

[75] Inventors: Leonard J. Buckley, Springfield, Va.; Greg Collins, Waldorf, Md.

[73] Assignee: The United States of America as represented by the Secretary of the Navy, Washington, D.C.

[21] Appl. No.: 543,412

[22] Filed: Oct. 16, 1995

[51] Int. Cl.[6] .................................................. G01N 27/12
[52] U.S. Cl. ........................... 436/151; 436/902; 422/90; 422/98; 338/34; 73/31.01; 73/31.05
[58] Field of Search ...................... 436/151, 902; 422/82.02, 83, 90, 98; 324/464; 338/34, 13; 73/31.01, 31.02, 31.05, 31.03

[56] References Cited

U.S. PATENT DOCUMENTS

| | | | |
|---|---|---|---|
| 4,794,365 | 12/1988 | Dunbar | 338/99 |
| 5,060,527 | 10/1991 | Burgess | 73/862.68 |
| 5,141,717 | 8/1992 | McRae | 422/82.01 |
| 5,145,645 | 9/1992 | Zakin et al. | 422/98 |
| 5,528,155 | 6/1996 | King et al. | 324/713 |

OTHER PUBLICATIONS

Fruend et al., "A chemically diverse conducting polymer based electronic nose", vol. 92, Proc. Natl. Acad. Sci. USA pp. 2652–2656 (Mar. 1995.
Gregory et al., Conductive Textiles, 28 Synthetic Metals C823–C835 (1989).
Kuhn et al., Toward Real Applications of Conductive Polymers, 71 Synthetic Metals 2139–2142 (1995.
J. Janata, 63 Awal. Chem. 2546 (1991).
Kunugi et al., J. Chem. Sco. Chem. Commun., pp. 873 (1994).
Josowicz et al., 58 Anal. Chem. 514 (1986).
McGill et al., 24 Chemtech 27 (1994).
Hanawa et al., Gas Sensitivity of Polypyrrole Films to $NO_2$, J Chem Soc., Trans. 1, 84 (5), pp. 1587–1592 (1992).
Grate et al., 65 Anal. Chem., 1868 (1993).
Buckley et al., Polymer—Analyte Interactions for Chemical Sensors based Upon Electro-active Polymer—Coated Fabric, abstract, p. 176, 42nd Nat. Symp., Oct. 16–20, 1995.
Aromascan, Intelligent Sensor Technology, Product Literature from Aromascan including Article from Wall Street Journal of Mar. 1, 1995 by Kyle Pope, (Author of Product Literature not identified).
Hodgins, D., The development of an Electronic "Nose" for Industrial and Environmental Applications, 13 page document, Product Literature from Neotronics Scientific.
Marsili, Ray, Electronic Noses Sniff Out New Aroma Applications, R&D Magazine, pp. 61–62 (Jul. 1995).
Nose, Product Literature from Notronics Scientific, 8 page document (Author not identified).
Greenfield, P., Aromascan sniffs out medical applications, Product Feature, 9 page document, Product Literature from Aromascan, Inc.

*Primary Examiner*—Jeffrey Snay
*Attorney, Agent, or Firm*—Thomas E. McDonnell; John Karasek

[57] ABSTRACT

A fabric chemical sensor, a process and an apparatus is disclosed. The sensor, process and apparatus are for the detection, classification, identification and/or quantitation of one or more component chemicals of a chemical vapor via a resistance measurment made across sensor in response to exposure of the sensor to the chemical vapor.

22 Claims, 9 Drawing Sheets

| Fabric Type | ΔR/R % | | | | |
|---|---|---|---|---|---|
| | Dry Air | 29 ppm NH$_3$ | 69 ppm NO$_2$ | 28 ppm DMMP | H$_2$O 60% Rel. Humidity |
| PP/NDSA/Nylon | 0.23 | 1.76 | -0.50 | -0.40 | -6.36 |
| PP/NDSA/PET | 0.55 | 3.82 | -0.45 | -0.31 | -8.92 |
| PP/AQSA/PET | 0.42 | 1.13 | -0.27 | -0.35 | -4.26 |
| PAN/Cl$^-$ | 0.17 | 7.41 | 13.7 | -0.09 | -107.6 |

*FIG. 8*

| Fabric Resistivity for PP/NDSA on PET | Exposure to 28 ppm DMMP in Dry Air | |
|---|---|---|
| | Resistivity Change (Signal/Noise) | Initial Response Slope (-ΔR/Δt/Noise, 1/min) |
| 211 ohms/cm$^2$ | 8.7 | 0.65 |
| 775 ohms/cm$^2$ | 59.4 | 3.53 |
| 3000 ohms/cm$^2$ | 50 | 8.42 |

*FIG. 9*

| Polymer Overcoat | ΔR/R % | | | |
|---|---|---|---|---|
| | 21 ppm NH$_3$ | 50 ppm NO$_2$ | 28 ppm DMMP | H$_2$O 10% Rel. Humidity |
| PP/NDSA Blank | 4.33 | -0.57 | -2.05 | -13.3 |
| FPOL Coated | 3.86 | -0.76 | -1.96 | -12.1 |
| PEI Coated | 0.12 | -0.88 | -2.01 | -29.4 |
| PIB Coated | 4.74 | -1.90 | -0.77 | -9.4 |
| SXFA Coated | 5.03 | — | -0.12 | -7.7 |

FIG. 10

CONDUCTIVE POLYMER COATED FABRICS FOR CHEMICAL SENSING

BACKGROUND OF THE INVENTION

1. Field of the Invention

The presently disclosed invention relates to an apparatus and method for the detection, differentiation, classification, identification and/or quantitation of one or more component chemicals of chemical vapors or various gases using a conductive polymer coated fabric chemical sensor. More particularly, the presently disclosed invention relates to an apparatus and method for detecting and measuring changes in the resistance of a fabric chemical sensor upon exposure of the sensor to chemical vapors and conveying that change in resistance into a "fingerprint" pattern of the chemical vapor for classification, identification and/or quantitation of one or more component chemicals of the chemical vapor.

2. Description of the Related Art

Plasticized poly(pyrrole) sensors for detecting vapors from various chemicals such as solvents (e.g. acetone, chloroform, isopropyl alcohol, methanol, ethanol, tetrahydrofuran, benzene and ethylacetate) are described by Fruend and Lewis. See Fruend, M. S. and Lewis, N. S., *A chemically diverse conducting polymer based "electronic nose"*, Vol. 92 *Proc. Natl. Acad. Sci. USA* pp. 2652–2656 (March 1995), incorporated herein by reference in its entirety and for all purposes. Fruend and Lewis describe an air stable sensor array of plasticized poly(pyrrole) elements fabricated upon interdigitated metal lines of a commercial 22-nF ceramic capacitor. Each of the elements of the sensor array consists of poly(pyrrole) and a plasticizer wherein the plasticizer composition is varied to obtain the different sensor elements. While the sensor array of Fruend and Lewis can distinguish between the vapors of various solvents, the use of an interdigitated ceramic capacitor contributes to a sensor array that is not very adaptable to varying environments, a sensor that is cumbersome and difficult to use, a sensor that is expensive to produce and possibly a sensor having little durability. In addition, the ceramic capacitors are inherently difficult to incorporate into useful articles.

In U.S. Pat. No. 5,145,645, incorporated herein by reference in its entirety and for all purposes, a chemical species detector is disclosed wherein the detector includes a conductive polymer based sensing element. The conductive polymer of U.S. Pat. No. 5,145,645 (hereinafter the '645 patent) is deposited on an electrically insulating supporting substrate which appear to be a rigid solid (depicted in FIG. 3 of the '645 patent and described at col. 6, lines 12–16). From FIG. 3 of the '645 patent, it appears that a conductive polymer section 14 is deposited on a portion of the underlying electrically insulating section 12, the conductive polymer layer being attached to electrodes 16 and 18, respectively.

A similar sensor is depicted in FIG. 1 of the article by T. Hanawa, S. Kuwabata, and H. Yoneyama entitled *Gas Sensitivity of Polypyrrole Films to $NO_2$* which is published in *J. Chem. Soc., Trans.* 1, 84(5), pp. 1587–1592 (1992), incorporated herein by reference in its entirety and for all purposes. The sensor is built on a rigid electrically insulating glass plate.

No sensors for measuring chemical resistance (or conductivity) are known to date having the flexibility, the strength, the surface area, the ease of production and the mechanical properties of a fabric. There is a need for a sensor for measuring chemical resistance (or conductance) wherein the sensor is formed from sensor elements comprised of fabric materials (e.g. woven fabrics). The incorporation of sensor elements into a fabric will impart the much needed mechanical strength, durability, flexibility, ease of production and incorporability into useful articles of a fabric to the sensor element.

SUMMARY OF THE INVENTION

It is therefore an object of the present invention to provide a fabric chemical sensor for detecting one or more chemical components of chemical vapors and/or gases wherein the sensor comprises one or more sensor elements built into a fabric.

It is therefore another object of the present invention to provide a fabric chemical sensor for detecting and/or quantitating one or more chemical components of chemical vapors and/or gases wherein the sensor comprises one or more sensor elements built into a fabric.

It is therefore still another object of the present invention to provide a fabric chemical sensor for detecting, classifying and/or quantitating one or more chemical components of chemical vapors and/or gases wherein the sensor comprises one or more sensor elements built into a fabric.

It is therefore yet another object of the present invention to provide a fabric chemical sensor for detecting, classifying, differentiating, identifying and/or quantitating one or more chemical components of chemical vapors and/or gases wherein the sensor comprises one or more sensor elements built into a fabric.

It is therefore even yet another object of the present invention to provide a sensor element comprising a fabric woven from insulating fibers coated with one or more conductive polymers, optionally doped with one or more dopants, and further optionally coated with one or more polymeric bilayers.

It is therefore a further object of the present invention to provide a sensor element comprising a fabric woven from insulating fibers coated with one or more conductive polymers selected from the group consisting of poly(pyrrole), poly(aniline) and mixtures thereof, the fibers being further doped with dopants selected from the group consisting of chloride ion, p-toluene sulfonic acid (PTSA), napthalene disulfonic acid disodium salt (NDSA), napthalene-2-sulfonic acid sodium salt (N2SA), anthraquinone-2-sulfonic acid sodium salt (AQSA) and mixtures thereof.

It is an even further object of the present invention to provide a sensor element comprising a fabric woven from insulating fibers being selected from the group consisting of polyethylene terephthalate (PET), nylon threads and mixtures thereof, the fibers coated with one or more conductive polymers selected from the group consisting of poly(pyrrole), poly(aniline) and mixtures thereof, the fibers being further doped with dopants selected from the group consisting of chloride, PTSA, NDSA, N2SA, AQSA and mixtures thereof.

It is even yet a further object of the present invention to provide a sensor element comprising a fabric woven from insulating fibers being selected from the group consisting of polyethylene terephthalate (PET), nylon threads and mixtures thereof, the fibers coated with one or more conductive polymers selected from the group consisting of poly(pyrrole), poly(aniline) and mixtures thereof, the fibers being further doped with dopants selected from the group consisting of chloride ion (chloride), PTSA, NDSA, N2SA, AQSA and mixtures thereof, and the doped-conductive polymer coated fibers further coated with a polymeric bilayer selected from the group consisting of polyethyleneimine (PEI), poly(isobutylene) (PIB), fluoroalcoholpolysiloxane (SXFA, or 1-(4-hydroxy, 4-trifluoromethyl, 5,5,5-trifluoro)pentene, methylpolysiloxane), fluoropolyol (FPOL, infra) and mixtures thereof.

It is still another object of the present invention to provide an apparatus and method for the detection, analysis, differentiation, classification, identification and/or quantitation of one or more component chemicals of chemical vapors and/or gases using a fabric chemical sensor further comprising one or more sensor elements wherein the sensor elements comprise conductive polymer coated fabrics with optional dopants and optional polymeric overcoats (i.e. bilayers).

These and other objects are accomplished by the process comprising the steps of:

(i) electrically connecting one or more fabric chemical sensors to a power source, said one or more fabric chemical sensors comprising one or more sensor elements, said sensor elements woven into a fabric of insulating fibers, said fibers being coated with one or more conductive polymers, each of said fabric chemical sensors having a baseline resistance;

(ii) exposing at time=$t_0$ over said one or more fabric chemical sensors a chemical vapor, said chemical vapor comprising one or more component chemicals;

(iii) detecting and quantifying a change in said baseline resistance of said one or more fabric chemical sensors at a later time=$t_1$ in response to exposure of said one or more fabric chemical sensors to said chemical vapor; and (iv) resolving and classifying from said change in said baseline resistance the identity of at least one of said one or more component chemicals of said chemical vapor.

The above process is accomplished by an apparatus comprising:

(i) one or more fabric chemical sensors further comprising one or more sensor elements, said one or more sensor elements being woven from insulating fibers, said fibers being coated with one or more conductive polymers;

(ii) a power supply being electrically connected to said one or more fabric chemical sensors, said one or more fabric chemical sensors having a measurable baseline resistance;

(iii) a means for exposing a chemical vapor over said one or more fabric chemical sensors sufficient to measure a reproducible change in said baseline resistance, said chemical vapor further comprising one or more component chemicals;

(iv) a means for detecting and quantifying said change in said baseline resistance in response to said exposure of said one or more fabric chemical sensors to said chemical vapor; and (v) a means for resolving from said change in said baseline resistance a classification of the identity of at least one of said one or more component chemicals of said chemical vapor.

BRIEF DESCRIPTION OF THE DRAWINGS

FIG. 8 is an exemplary table of $\Delta R/R$ % readings for various fabric chemical sensor types upon exposure to various chemical vapors (i.e. various gas vapors) as indicated.

FIG. 9 is an exemplary table of change in resistivity and initial response slope of various fabric thicknesses (i.e. various fabric thicknesses can be correlated to various baseline resitivities of exemplary NDSA doped-poly (pyrrole) conductive polymer coated onto PET fibers woven into fabric chemical sensors) upon exposure to DMMP (28 ppm in dry air).

FIG. 10 is an exemplary table of $\Delta R/R$ % readings for various fabric chemical sensor types coated with various polymer overcoats (as indicated) upon exposure to various chemical vapors (i.e. various gas vapors) as indicated.

DETAILED DESCRIPTION OF THE PREFERRED EMBODIMENTS

Figure 1:
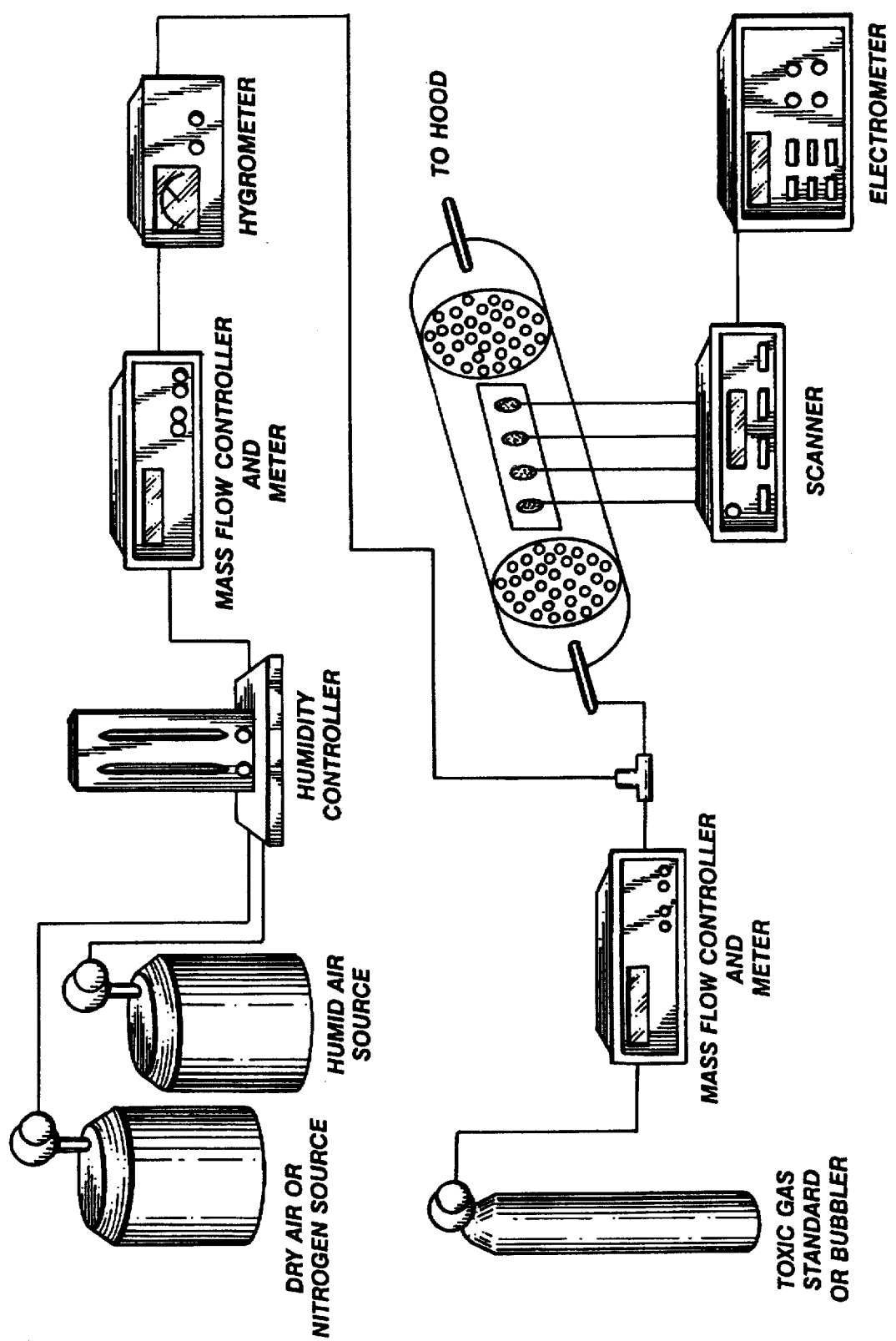
FIG. 1 is a schematic diagram of an exemplary setup of apparatus for simultaneously characterizing the response of four fabric chemical sensors to exposure to gas vapors.

Conductive polymers are an effective medium for chemical sensing, based upon electronic changes arising in the polymeric films with the gas phase adsorption of electronically active vapors. The conductivity changes observed in these polymers are attributed to the interaction of electronically active analytes with either the polymer backbone itself, or the dopant molecules incorporated within the film, thereby modulating the mobility and/or number of free charge carriers available.

According to the present invention, a format for forming and utilizing fabric chemical sensors for the detection of one or more component chemicals within chemical vapors is disclosed. Broadly, insulating fibers are coated with one or more conductive polymers which conductive polymers may be optionally doped with one or more dopants and further optionally coated with an overcoat polymer layer (i.e. bilayer polymer). These fibers are woven into a fabric and connected to a power source to measure a baseline resistance across the fabric chemical sensor (e.g. the sensor woven from exemplary doped-conductive polymer coated fibers having an optional polymer overcoat). After measuring a baseline resistance, an exemplary array of fabric chemical sensors is exposed to a chemical vapor and a change in the baseline resistance is detected and measured to form a "fingerprint" pattern for the chemical vapor. Typically, the "fingerprint" pattern is obtained by exposing a plurality of fabric chemical sensors (of various dopants, fiber thicknesses, fiber compositions and polymer overcoats, respectively) to the chemical vapor. The "fingerprint" pattern so obtained is analyzed to identify, classify, and/or quantify one or more component chemicals present within the chemical vapor tested.

Exemplary insulating fibers used according to the present invention include nylon and PET. However, any insulating fiber that can be readily woven into a fabric and accept a coating of a conductive polymer may be used in accordance with the present invention.

Exemplary conductive polymers used according to the present invention include poly(pyrrole) and poly(aniline). However, any conductive polymer that can be polymerized onto insulating fibers (the fibers suitable for weaving into fabrics) may be used. Preferably, a suitable conductive polymer will incorporate dopant anions such as NDSA, AQSA and chloride. More preferably, a suitable conductive polymer will also permit deposition of a polymer overcoat such as polyethyleneimine (PEI), fluoroalcoholpolysiloxane (SXFA, or 1-(4-hydroxy, 4-fluoromethyl, 5,5,5-trifluoro) pentene, methylpollysiloxane) and fuoropolyol (FPOL), FPOL having the structure fabric filaments woven into fabrics with conductivities that 1) are uniform over the length of the material, 2) can be varied over a wide range of values, 3) are stable over long time periods, and 4) combine the electrical properties of the conductive polymer coating with the mechanical properties of the fabric. See Kuhn et al., *Toward Real Applications of Conductive Polymers*, 71 Synthetic Metals 2139–2142 (1995), incorporated herein by reference in its entirety and for all purposes. See also Gregory et al., *Conductive Textiles*, 28 Synthetic Metals C823–C835 (1989), incorporated herein by reference in its entirety and for all purposes.

Figure 2:
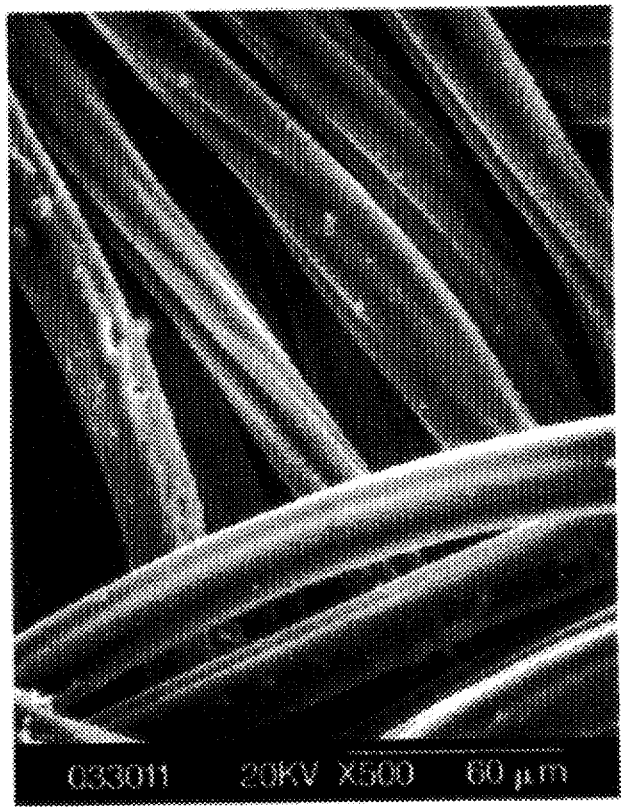
FIG. 2 is a scanning electron microscope image (SEM) taken of a NDSA-doped poly(pyrrole) conductive polymer on PET woven fibers at a magnification of 500×, the image depicting the nature of the fabric weave and the character of the conductive polymer coating.

Scanning electron microscope (SEM) images taken of exemplary fabric weaves demonstrate the pristine nature of the chemically gown, polymeric films. Shown in FIG. 2 is an SEM image taken of an exemplary NDSA-doped poly (pyrrole) film on polyethylene terephthalate (PET) using an electron voltage of 20 kV and a magnification of 500×. The chemical deposition of the poly(pyrrole) resulted in a smooth, even overlayer on the PET thread, although there do exist regions where the polymer aggregated during polymerization. The fabric weave consists of a series of overlapping, conductive polymer-coated threads, which results in a much more complicated, fabric chemical sensor substrate than that found for films grown on chemiresistor devices, quartz crystal microbalances or field effect transistors, for example. If we presume that the conduction process in poly(pyrrole) and poly(aniline) operates according to a p-type, hole-hopping mechanism, the conduction path for a single hole might be expected to traverse several threads. The swelling of conductive polymers due to gas analyte adsorption will generate considerable changes in the transport pathways of free charge carriers within these films. Exemplary high levels of doping in conductive polymers (e.g. 10–30%) make the dopant anion an important consideration in defining the sensor response of each conductive polymer-coated fabric.

To assess the relative thermal stability of the exemplary conductive polymer coatings on the exemplary PET thread, thermal gravimetry analysis (TGA) was performed on several exemplary fabric weaves. Thermogravimetry analysis (TGA) was performed in air using a Perkin Elmer TGA-7

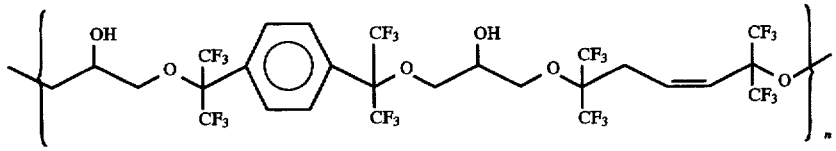

where n=5, 6, 7, 8, 9, or 10.

Conductive polymer-coated fabric characteristics

Figure 3:
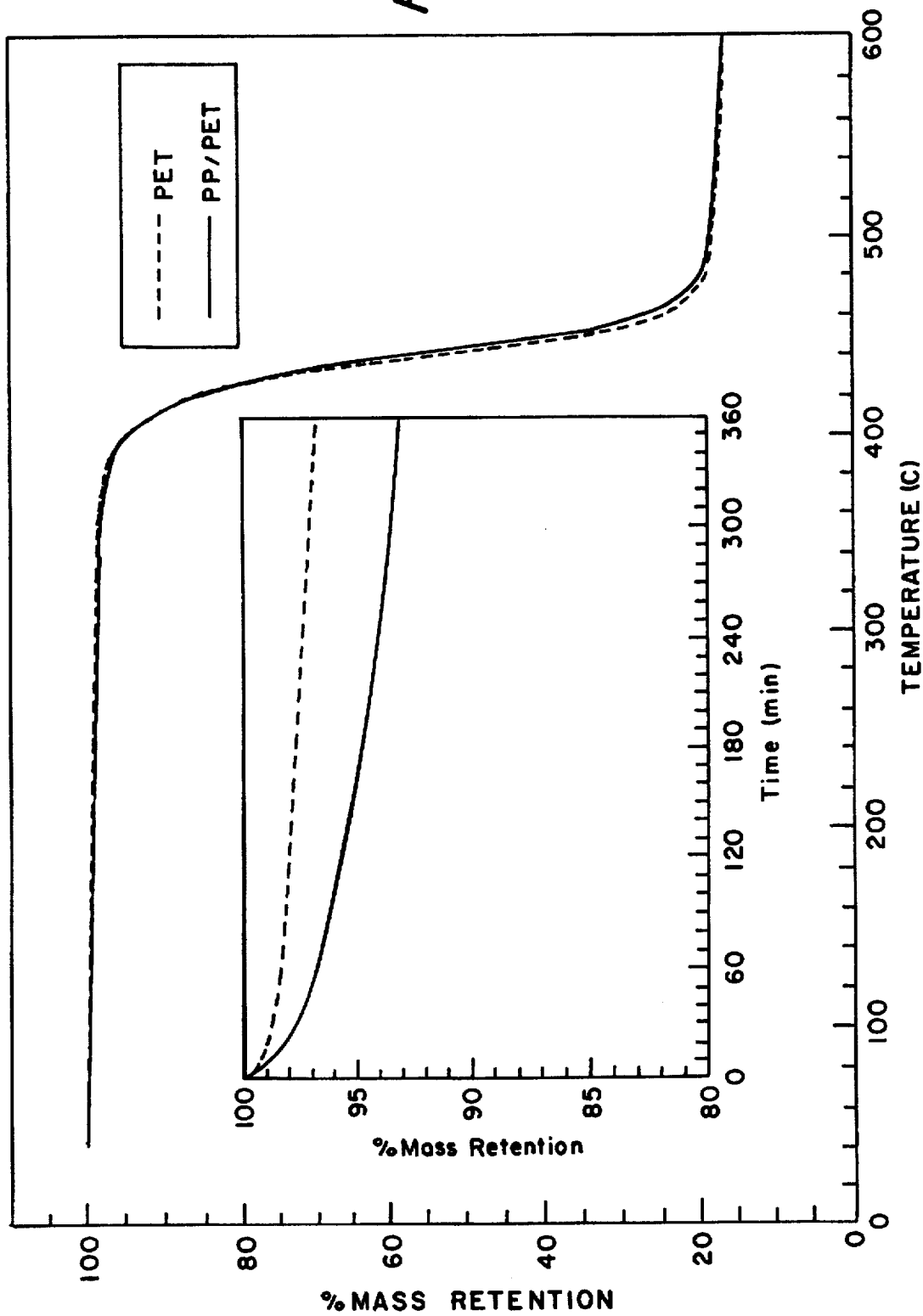
FIG. 3 is a scanning thermo-gravemetric analysis (TGA) plot recorded of PET fibers (dashed lines) and poly(pyrrole)-coated PET fibers (solid lines), respectively. The inset is an isothermal TGA (300° C. in air) plot taken of PET fibers (dashed lines) and poly(pyrrole)-coated PET fibers (solid lines), respectively.

The conductive polymer-coated fabrics used consisted of exemplary weaved fiber filaments coated with conductive polymer overlayers, grown by chemical polymerization or oxidative coupling of the exemplary monomer, pyrrole or aniline. The dopant anion, e.g. naphthalene disulfonic acid (NDSA), anthraquinone-2-sulfonic acid (AQSA) or Cl⁻, was simultaneously incorporated into the conductive polymer chain, giving the polymer network its conductivity. The conductive polymers were typically coated onto the fiber filaments by an in situ solution polymerization process that is based on oxidative coupling of the monomer species (e.g. pyrrole or aniline) and simultaneous incorporation of the dopant. See Gregory et al., 28 Synthetic Metals, C823–C835 (1989), incorporated herein by reference in its entirety and for all purposes. The in situ process permits the controlled growth of relatively thin films of conductive polymers on analyzer under both isothermal (300° C.) and scanning conditions (10° C./sec). A scanning TGA plot of exemplary PET and poly(pyrrole) coated PET fibers in air is shown in FIG. 3. The degradation curves for these two materials are essentially identical, maintaining nearly 100% mass retention up to 380° C., before dropping off over the course of 100° C. and leveling off at ~20% mass retention above 500° C. Shown in the inset of FIG. 3 is an isothermal TGA (300° C. in air) plot for a similar set of exemplary PET and poly(pyrrole) coated PET fibers. In this plot, we can differentiate the loss mechanisms apparent in PET from those of the poly(pyrrole) overcoat. The thermal stability of these films suggests the possibility of utilizing temperature as an additional parameter for improving selectivity and recovery time in fabric-based chemical sensors.

Analytical characterization of the fabric weaves was undertaken to improve our understanding of the film's interfacial properties. X-ray photoelectron spectroscopy (XPS) measurements were conducted using a Surface Science spectrometer. The XPS spectra were collected using AlKα non-monochromatized radiation and a hemispherical analyzer in the constant analyzer energy mode with a pass energy of 20 eV. A Hitachi Field Emission scanning electron microscope (SEM) operating at an electron voltage of 20–25 kV was used to obtain images of the conductive polymer-coated fabrics. Because of the conductive properties associated with these fabric weaves, it was not necessary to generate an electrically conductive overcoat.

Conductive polymer-coated fabrics

Unless mentioned otherwise, all fabrics were used as received from the manufacturer. Exemplary conductive polymer-coated fabrics were acquired from Milliken Research Corp., and included 1) poly(pyrrole) on a 150 denier poly(ethylene) terephthalate (PET) doped with naphthalene disulfonic acid (NDSA)-available resistivities included 211, 775, and 3000 ohms/$cm^{2}$; $^{2}$) poly(pyrrole) on a 150 denier PET doped with anthraquinone-2-sulfonic acid (AQSA)- resistivity 129 ohms/$cm^{2}$; $^{3}$) poly(pyrrole) on a 840 denier nylon doped with NDSA- resistivity 100 ohms/$cm^{2}$; and, 4) poly(aniline) on a 150 dealer PET doped with $Cl^{31}$- resistivity 75 ohms/$cm^{2}$. For all chemical sensing experiments, a 12 $cm^2$ square piece of fabric was cut from a sheet of the conductive polymer-coated fabric, and a thin line of silver paint (Alfa Aesar) was applied to opposite ends of the fabric and allowed to dry. An additional, small amount of silver paint was then utilized for making an electrical connection between a teflon-coated wire and the opposing sides of the fabric. After drying overnight, the fabric swatches were placed within the testing apparatus and allowed to equilibrate in a stream of dry air.

Apparatus and instrumentation

Shown in FIG. 1 is a diagram of an exemplary experimental configuration employed for examining the chemical sensing characteristics of the coated fabric materials (i.e. fabric chemical sensors). Four fabric swatches were examined simultaneously by positioning them within a teflon (PTFE, Dupont) support containing four exposure holes (2 cm diameter). The teflon support was contained within a 0.5 liter glass chamber which held a set of baffled, teflon discs at the front and back of the chamber in order to promote laminar flow across the fabric surface. Air flow within the testing chamber was maintained using Matheson Model 8200 series mass flow controllers at a constant flow rate of either 1 l/min or 10 l/min. Given a cross-sectional area of 23.8 $cm^2$, the face velocities were calculated to be between 42 and 420 cm/min (1.4–14 ft/min), velocities that closely approximate exchange rates in typical indoor environments. Gas standards containing 450 ppm $NH_3$ in $N_2$ and 1053 ppm $NO_2$ in $N_2$ were obtained from Matheson, Inc. and Potomac Airgas, Inc., respectively. Dimethyl methylphosphonate (DMMP) was acquired from Aldrich, Inc., and placed within a bubbler held at a constant temperature of 15° C. using a temperature controlled water bath manufactured by GCA, Inc. Previous studies have calibrated the DMMP bubbler to generate ~2960 mg of DMMP per $m^3$ while being maintained at this temperature. See Grate et al., 65 Anal. Chem., 1868 (1993), incorporated herein by reference in its entirety and for all purposes. Humidity was controlled via the use of bubblers and line mixers, and quantitated using a Hygrodynamics hygrometer. All resistivity measurements were made using a Keithley 617 programmable electrometer (at an applied potential of 0.0946 V) and a Keithley 705 scanner which enabled the sequential sampling of the resistivity for each of the conductive polymer-coated fabrics held within the testing chamber. National Instruments' LabView for Windows controlled the data acquisition across an AT-GPIB interface board.

Fabric response to $NH_3(g)$ and $NO_2(g)$

Figure 4:
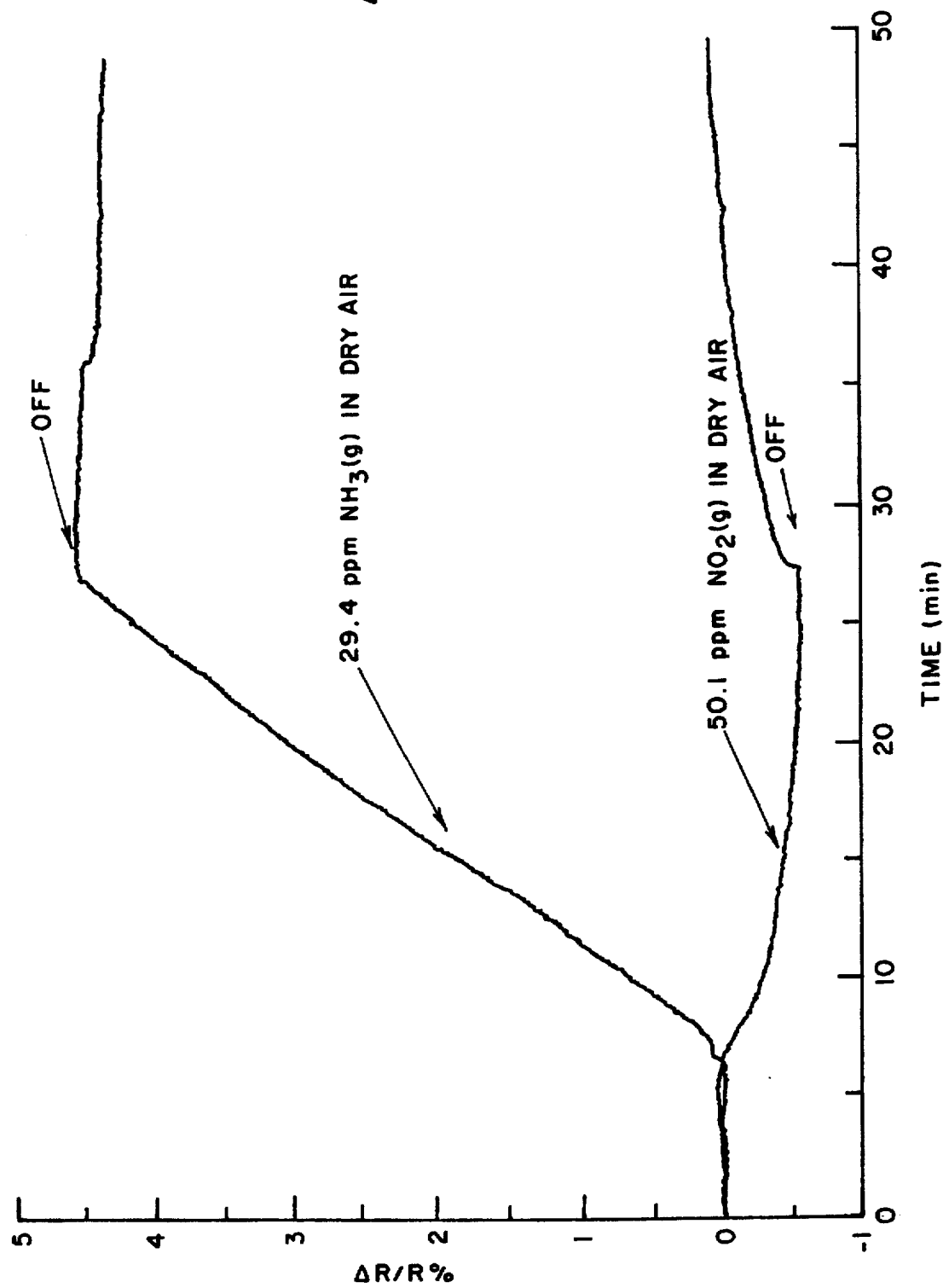
FIG. 4 is an exemplary plot of $\Delta R/R$ % (wherein $\Delta R$ is the change in the resistance from baseline resistance measured prior to exposure of fabric chemical sensor to chemical vapor(s) and R is the baseline resistance). A change in the resistivity is observed from an NDSA-doped poly(pyrrole) conductive polymer coated onto PET fibers (woven into a fabric chemical sensor) to $NH_3(g)$ (29.4 ppm) exposure and $NO_2(g)$ (50.1 ppm) exposure, in air, respectively.

The conductive polymer-coated fabric weaves were initially exposed to ppm levels of $NH_3(g)$ and $NO_2(g)$, in order to assess the responsivity of these materials to toxic gases known to interact electronically with conductive polymer, thin films. Shown in FIG. 4 is a plot of the change in resistivity for a NDSA doped poly(pyrrole) film on PET upon the introduction and cessation of 29.4 ppm $NH_3(g)$ and 50.1 ppm $NO_2(g)$ in a stream of dry air. For NDSA doped poly(pyrrole) films on fabric, 1) ammonia resulted in an increase in the resistivity which was nearly linear with time and essentially irreversible; while 2) nitrogen dioxide caused a monotonic decrease in the resistivity which was reversible in its response. The fabric shown in FIG. 4 was found to be nearly 14 times more sensitive to the detection of ammonia, when Compared to nitrogen dioxide, although both have demonstrated responses in the low ppm regime.

Because conductive polymers are generally acknowledged to exhibit behavior which is in accordance with p-type conductive materials, it is reasonable to expect that 1) $NH_3(g)$, a strong reductant, will result in a decrease in the conductivity due to the elimination of free hole charge carriers, while 2) $NO_2(g)$, a strong oxidant, will cause an increase in the conductivity due to the formation of additional, free hole charge carriers within the film.

FIG. 8 summarizes the $\Delta R/R$ percent changes measured for four different, conductive polymer-coated fabrics upon exposure to the various gases examined as indicated. The first two fabric weaves consisted of the same dopant and conductive polymer type (PP/NDSA), differing only in the thread substrate (PET or nylon). The third fabric also consists of poly(pyrrole) on PET, but in this case the dopant was AQSA. The final material was weaved from PET fibers coated with $Cl^-$ doped poly(aniline). Focussing on the results obtained for $NH_3(g)$ and $NO_2(g)$, we note that the direction of the resistivity changes matched the expected responses, with the exception of the $Cl^-$ doped poly(aniline) on PET fabric's response to $NO_2(g)$. Of the two dopants utilized for the poly(pyrrole) films, NDSA and AQSA, NDSA reported the largest signal with respect to the detection of $NH_3(g)$ and $NO_2(g)$.

The role $O_2(g)$ must also be considered on defining the conductivity of these materials. For each of the fabric weaves investigated, the introduction of pure $O_2(g)$ (1 l/min) to a film equilibrated in an inert atmosphere of nitrogen, resulted in a small but steady increase in the resistivity that leveled off after several hours of exposure (~2%). Under normal atmospheric conditions (20% oxygen levels), it is expected that the surface of these exemplary fabric swatches (i.e. fabric chemical sensors) will be electronically perturbed by the chemisorption of oxygen onto the surface of the conductive polymer. Because of this interaction, an additional factor to consider in assessing the resistivity changes observed in these materials, is the displacement of weakly chemisorbed $O_2(g)$ molecules by competing analytes within the air stream- a displacement of the $O_2(g)$ molecules will cause a resultant decrease in the resistivity of the film. In addition to the reversible response of oxygen with the surface of these fabric weaves, there is a slow, irreversible decay in the conductivity (i.e. increase in resistivity) linked to the degradation of the conductive polymer via a reaction between oxygen and the polymer backbone that gives rise to the formation of non-conjugated moieties. See J. Janata, 63 Anal. Chem. 2546 (1991), incorporated herein by reference in its entirety and for all purposes.

Response to Chemical Warfare Agent Simulant (DMMP)

Figure 6:
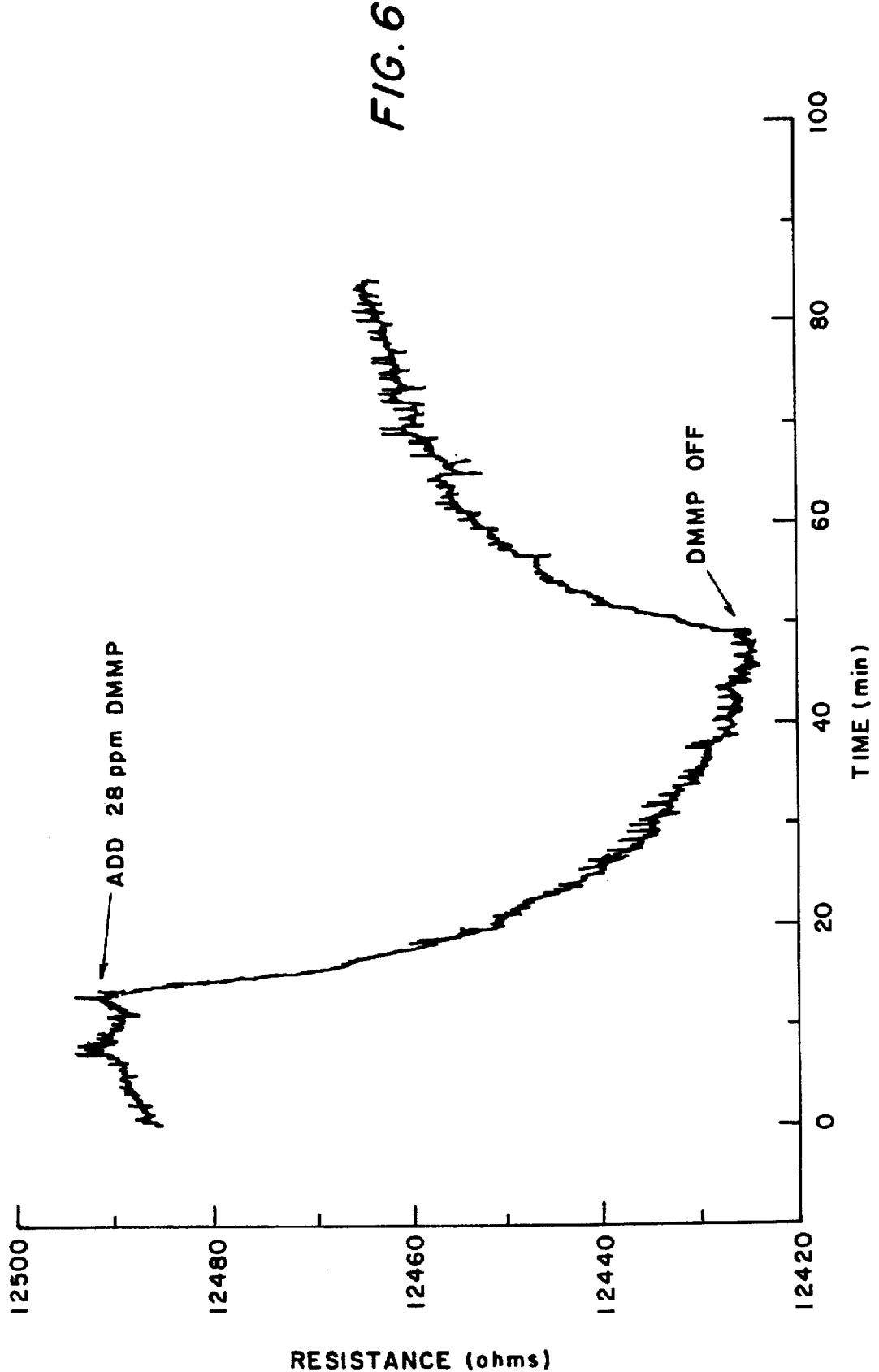
FIG. 6 is an exemplary plot of resistance (ohms) versus time (minutes) for an NDSA-doped poly(pyrrole) conductive polymer coated onto PET fibers (woven into a fabric chemical sensor) to exposure to dimethyl methylphosphonate (DMMP) (28 ppm) in dry air.

In order to investigate the feasibility of using the electroactive polymer coated fabric materials for the detection of chemical warfare agents, a series of experiments were designed to examine the responsivity of the fabrics to an organophosphonate, chemical warfare agent simulant, dimethyl methylphosphonate (DMMP). A typical response curve obtained for the introduction of 28 ppm DMMP in dry air to a NDSA doped poly(pyrrole) on PET fabric is shown in FIG. 6. DMMP interacts electronically with the polymer, generating a resistivity drop that is responsive in the low ppm regime. Apparently, DMMP interacts with the conductive polymer to increase the quantity of free and mobile hole charge carriers. The response observed for the fabric materials is reversible and somewhat dependent upon the dopant and conductive polymer type, as well as the substrate material (see FIG. 8). The chloride ion doped poly(aniline) was not nearly as sensitive to DMMP, despite having responded so well to the other vapors studied here.

The NDSA doped poly(pyrrole) fabric was further examined for the detection of DMMP wherein attention was focussed on the properties of the conductive polymer for improving DMMP detection. More specifically, the effect of film thickness on response time and responsivity to DMMP were examined in a set of three different NDSA doped poly(pyrrole) on PET fabrics (see FIG. 9). The three materials differed according to their inherent surface resistance, a factor which was not a feature of the extent of doping, 4 but rather a measure of the film thickness. Qualitatively, the thickness of the conductive polymer films decreased in the order 3000>775>211 ohms/cm$^2$. Examining first the magnitude of response to the introduction of 28 ppm DMMP in dry air, the best signal-to-noise ratio was attained for the 775 ohm/cm$^2$ film, although the 3000 ohms/cm$^2$ was nearly as sensitive. The speed of response, however, was most rapid in the 3000 ohms/cm$^2$ film, as evidenced by the initial response slope recorded upon the introduction of DMMP. In addition, the mobile charge carriers generated by the adsorption of a single molecule of DMMP are more easily detected in films possessing lower conductivities. The 775 ohms/cm$^2$ poly(pyrrole) coated material was selected for all further investigations.

The response of the conductive polymer-coated fabrics to DMMP within a carrier stream of dry air demonstrated the possibility for utilizing these materials for the detection of ppm levels of chemical warfare agents. Unfortunately, the same sensitivity was not observed for fabrics supported within a carrier stream of humid air. Following equilibration of the material's conductivity within any given humidity, the addition of DMMP failed to generate a measurable change in the resistivity. This was in contrast to the addition of NH$_3$(g) in humid air, which caused an identical resistivity change in the film to that seen in dry air. Apparently the chemisorption of DMMP to the conductive polymer surface is relatively weak, and, as a result, the DMMP is unable to displace water molecules from surface sites which were previously accessible under dry conditions.

Influence of humidity on conductivity

Figure 5A:
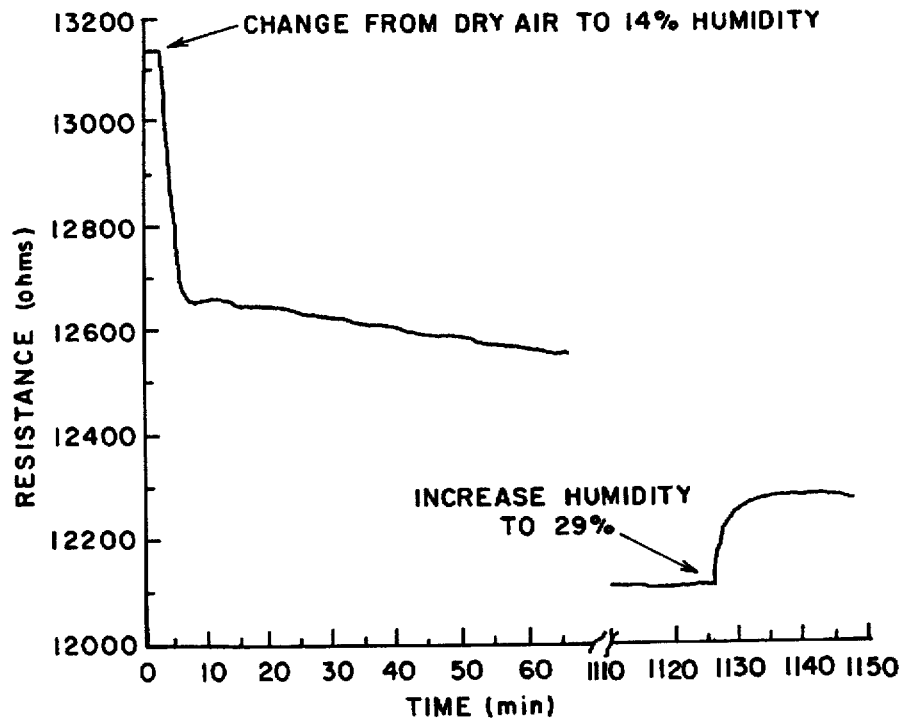
FIG. 5A is an exemplary plot of resistance (ohms) versus time (minutes) for an NDSA-doped poly(pyrrole) conductive polymer coated onto PET fibers (woven into a fabric chemical sensor) to increases in relative humidity from 0% to 14% to 29%.
Figure 5B:
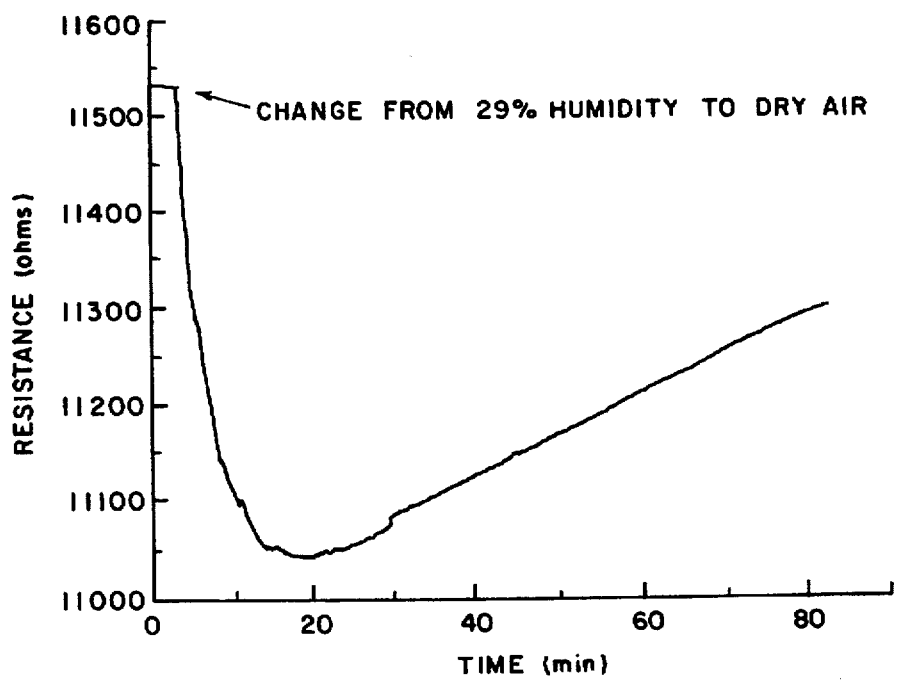
FIG. 5B is an exemplary plot of resistance (ohms) versus time (minutes) for an NDSA-doped poly(pyrrole) conductive polymer coated onto PET fibers (woven into a fabric chemical sensor) to decreases in relative humidity from 29% to dry air (0% relative humidity).

Humidity strongly influenced the conductivity level apparent in the conductive polymer-coated fabric weaves. With the exception of the Cl$^-$ doped poly(aniline) on PET fabric, which reported only a decrease in the resistivity, each of the exemplary fabric chemical sensors studied reported a dual response in the resistivity to increasing levels of humidity. FIG. 5a illustrates the change in resistivity seen for a NDSA doped poly(pyrrole) film on PET upon the introduction and equilibration of two increasing levels of humidity, 14% and 29%. When the fabric's environment was changed from a stream of dry air to a stream of humid air, the resistivity underwent a rapid decrease in the resistivity, which maintained a slow but steady decline for hours. Following equilibration, the resistivity increased slightly for all subsequent increases in the humidity. This dual response to humidity is mirrored in the resistivity changes seen for the conductive polymer-coated fabrics following a switch from a humid carrier stream to dry air (see FIG. 5b). As expected, the immediate response is a dramatic decrease in the resistivity, which is followed shortly by a gradual increase in resistivity.

Shown in FIG. 8 are the magnitudes of the negative, resistivity changes recorded upon the introduction and equilibration of 60% humidity for several different fabric materials. The Cl$^-$ doped poly(aniline) on PET responded to increasing humidity levels with monotonic decreases in the resistivity. In addition to lacking the dual response reported by the poly(pyrrole) based fabrics, the poly(aniline) coated fabric was more than 10 times as sensitive to humidity.

Polymer bilayers

Bilayer films, or polymer coatings deposited onto the surface of the conductive polymer-coated fabrics, were investigated for two reasons: 1) to investigate the feasibility of improving sensitivity and selectivity to a given analyte by coating the conductive polymer with a sorbent coating bearing particular functionality groups and properties which favor the adsorption of certain molecules over others; and 2) to coat the conductive polymer film with a hydrophobic coating which would maintain its responsivity to the analyte of interest while avoiding problems associated with the chemisorption of water vapor onto the conductive polymer surface. FPOL, SXFA, PEI and PIB sorbent polymers (i.e. bilayers) were used as coatings on exemplary fabric chemical sensors.

Polymer bilayer deposition

Optional polymeric overcoats (i.e. bilayer films) were deposited on the conductive polymer-coated fabrics by either spraying or dip-coating. Polyethyleneimine (PEI) was obtained from Phase Separations, Inc. and poly(isobutylene) (PIB) from Aldrich, Inc. Fluoroalcoholpolysiloxane (SXFA, or 1-(4-hydroxy, 4-trifluoromethyl, 5,5,5-trifluoro)pentene, methylpolysiloxane) was prepared and donated by Dr. Andrew McGill of Geo-Centers. See Kunugi et al., *J. Chem. Sot:. Chem. Commun.*, pp. 873 (1994), incorporated herein by reference in its entirety and for all purposes. Fluoropolyol (FPOL, supra), an oligomer, was synthesized in-house by Dr. Jim Griffith of the Naval Research Laboratory. See Josowicz et al., 58 *Anal Chem.* 514 (1986), incorporated herein by reference in its entirety and for all purposes. See also McGill et al., 24 *CHEMTECH* 27 (1994), incorporated herein by reference in its entirety and for all purposes. For those films prepared by spray-coating, a Badger Model 200-3 Air Brush was used to exhaustively spray 15 ml of a 0.7% solution of the polymer dissolved in chloroform onto the fabric swatch. For those films prepared by dip-coating, 33% (FPOL) and 11% (SXFA) solutions were prepared in butyl acetate, with the polymer uptake by the fabric being monitored gravimetrically. In order to drive off any excess solvent, the dip-coated fabrics were pumped under dynamic vacuum (1 mm) at 50° C. for 24 hours.

Figure 7:
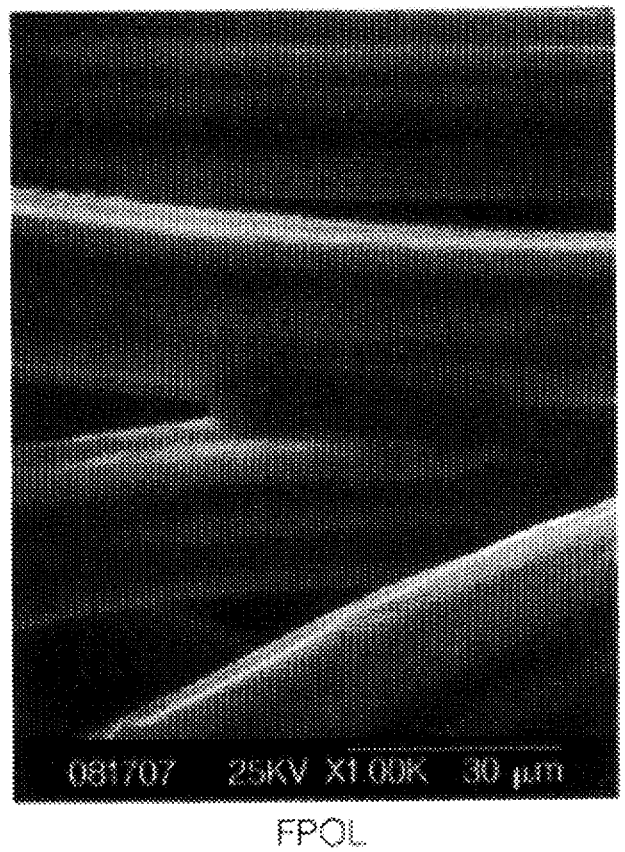
FIG. 7 is a scanning electron microscope image (SEM) taken of a NDSA-doped poly(pyrrole) conductive polymer on PET woven fibers further coated with a thin layer of fluoropolyol (FPOL) at a magnification of 1000×, the image depicting the nature of the fabric weave and the character of the conductive polymer coating.

Two methods were utilized for coating the fabric weaves with a thin coating of polymer: spraying and dip-coating. In order to ensure the quality of the film deposited, the films were characterized by XPS and SEM. Shown in FIG. 7 is a SEM taken of a NDSA doped poly(pyrrole) film on a PET fabric weave which was dip-coated with 0.33 g/cm$^3$ of FPOL. The deposition resulted in a smooth film, which coagulates in certain areas, literally connecting two fibers together, as can be seen in FIG. 7. XPS analysis verified the presence of the FPOL coating on the surface of the conductive polymer coated weave via the loss of the nitrogen 1s electron peak associated with the poly(pyrrole). The XPS data combined with the SEM analysis indicated the deposition of a smooth overlayer of FPOL which completely coated the poly(pyrrole) underlayer.

FIG. 10 summarizes the relative resistivity changes recorded for the blank and each of the bilayer films to the different gases within a carrier stream of dry air as indicated. With regards to the introduction of water vapor (10% humidity), the film exhibiting the largest decrease in resistivity was the PEI coated film. For the detection of $NH_3(g)$, the PEI film which exhibited the smallest change in its resistivity. In contrast, the SXFA coated fabric displayed the largest increase in resistivity due to the strong chemical sorption of $NH_3(g)$.

With respect to detection of DMMP, the worst signal response was observed for the SXFA coated fabric. It is further noted that the FPOL and PEI films caused little to no effect on their response to DMMP, while the PIB film caused a decrease in the resistivity change. Despite the presence of these sorbent polymer coatings, humidity still resulted in a complete swamping out of the signal generated by DMMP.

For the detection of $NO_2(g)$, the PEI coated film was more sensitive to $NO_2(g)$ than either the FPOL-coated fabric or the blank.

What is claimed is:

1. A process for the detection of one or more component chemicals of a chemical vapor, said process comprising the steps of:
    (i) electrically connecting one or more fabric chemical sensors to a power source, said one or more fabric chemical sensors comprising one or more sensor elements, said sensor elements woven into a fabric of insulating fibers, said fibers being coated with one or more conductive polymers, each of said fabric chemical sensors having a baseline resistance;
    (ii) exposing at time=$t_0$ over said one or more fabric chemical sensors a chemical vapor, said chemical vapor comprising one or more component chemicals;
    (iii) detecting and quantifying a change in said baseline resistance of said one or more fabric chemical sensors at a later time=$t_1$ in response to exposure of said one or more fabric chemical sensors to said chemical vapor; and
    (iv) resolving and classifying from said change in said baseline resistance the identity of at least one of said one or more component chemicals of said chemical vapor.

2. The process of claim 1 wherein said power source is a direct current battery, wherein said insulating fiber is selected from the group consisting of PET, nylon and mixtures thereof, and wherein said conductive polymer is selected from the group consisting of poly(pyrrole), poly (aniline) and mixtures thereof.

3. The process of claim 1 wherein said detecting and quantifying is accomplished using an electrometer and wherein said resolving and classifying is accomplished using a means for data acquisition.

4. The process of claim 3 wherein said means for data acquisition is a data acquisition algorithm.

5. The process of claim 1 wherein said one or more conductive polymers are doped with one or more dopants.

6. The process of claim 5 wherein said one or more dopants are selected from the group consisting of PTSA, NDSA, N2SA, AQSA, chloride ion and mixtures thereof.

7. The process of claim 5 wherein said one or more conductive polymers are coated with one or more bilayer polymers.

8. The process of claim 7 wherein said one or more bilayer polymers are selected from the group consisting of PEI, PIB, SXFA, FPOL and mixtures thereof.

9. An apparatus for the detection of one or more component chemicals of a chemical vapor, said apparatus comprising:
    (i) one or more fabric chemical sensors comprising one or more sensor elements, said one or more sensor elements being woven into a fabric of insulating fibers, said fibers being coated with one or more conductive polymers;
    (ii) a power supply being electrically connected to said one or more fabric chemical sensors, said one or more fabric chemical sensors having a measurable baseline resistance;
    (iii) a means for exposing a chemical vapor over said one or more fabric chemical sensors sufficient to measure a reproducible change in said baseline resistance, said chemical vapor further comprising one or more component chemicals;
    (iv) a means for detecting and quantifying said change in said baseline resistance in response to said exposure of said one or more fabric chemical sensors to said chemical vapor; and
    (v) a means for resolving from said change in said baseline resistance a classification of the identity of at least one of said one or more component chemicals of said chemical vapor.

10. The apparatus of claim 9 wherein said one or more conductive polymers are doped with one or more dopants.

11. The apparatus of claim 10 wherein said one or more dopants are selected from the group consisting of PTSA, NDSA, N2SA, AQSA, chloride ion and mixtures thereof.

12. The apparatus of claim 10 wherein said one or more conductive polymers are coated with one or more bilayer polymers.

13. The apparatus of claim 12 wherein said one or more bilayer polymers are selected from the group consisting of PEI, PIB, SXFA, FPOL and mixtures thereof.

14. The apparatus of claim 9 wherein said insulating fibers are selected from the group consisting of PET, nylon and mixtures thereof.

15. The apparatus of claim 14 wherein said conductive polymers are selected from the group consisting of poly (pyrrole), poly(aniline) and mixtures thereof.

16. The apparatus of claim 15 wherein said power supply is a direct current battery.

17. The apparatus of claim 16 wherein said means for exposing is one or more fabric chemical sensors exposed to ambient atmosphere.

18. The apparatus of claim 17 wherein said means for detecting and quantifying is an electrometer.

19. The apparatus of claim 18 wherein said means for resolving is an artificial neural network.

20. The apparatus of claim 18 wherein said means for resolving is a pattern selectivity algorithm.

21. The apparatus of claim 18 wherein said means for resolving is a means for data acquisition.

22. The apparatus of claim 21 wherein said means for data acquisition is a data acquisition algorithm.

* * * * *